US009289485B2

(12) United States Patent
Guglielmi et al.

(10) Patent No.: US 9,289,485 B2
(45) Date of Patent: Mar. 22, 2016

(54) **THERAPEUTIC APPLICATION OF *S. PYOGENES* C-TERMINAL PEPTIDE**

(71) Applicants: Luiza Guilherme Guglielmi, Sao Paulo (BR); Jorge Elias Kalil Filho, Sao Paulo (BR)

(72) Inventors: Luiza Guilherme Guglielmi, Sao Paulo (BR); Jorge Elias Kalil Filho, Sao Paulo (BR)

( * ) Notice: Subject to any disclaimer, the term of this patent is extended or adjusted under 35 U.S.C. 154(b) by 0 days.

(21) Appl. No.: 14/171,299

(22) Filed: Feb. 3, 2014

(65) Prior Publication Data

US 2014/0220065 A1   Aug. 7, 2014

Related U.S. Application Data

(63) Continuation-in-part of application No. 12/516,754, filed as application No. PCT/BR2007/000184 on Jul. 19, 2007, now Pat. No. 8,642,049.

(30) Foreign Application Priority Data

Nov. 30, 2006   (BR) ..................................... 0604997

(51) Int. Cl.
*A61K 39/09* (2006.01)
*A61K 39/00* (2006.01)

(52) U.S. Cl.
CPC ........... *A61K 39/092* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 6,063,386 A * | 5/2000 | Dale et al. ................... | 424/244.1 |
| 6,358,704 B1 | 3/2002 | Holmes et al. | |
| 6,419,932 B1 * | 7/2002 | Dale .......................... | 424/244.1 |
| 6,602,507 B1 | 8/2003 | Fischetti | |
| 6,716,433 B1 | 4/2004 | Dale | |
| 8,642,049 B2 * | 2/2014 | Guglielmi et al. ......... | 424/244.1 |
| 2002/0176863 A1 | 11/2002 | Dale | |
| 2005/0002956 A1 | 1/2005 | Lowell et al. | |

FOREIGN PATENT DOCUMENTS

| | | | |
|---|---|---|---|
| BR | PI 0501290-2 A | 12/2005 | |
| WO | 89/09064 A1 | 10/1989 | |
| WO | 90/15872 A1 | 12/1990 | |
| WO | 94/06465 A1 | 3/1994 | |
| WO | WO 94/06465 A1 * | 3/1994 | |
| WO | 2004/014956 A1 | 2/2004 | |

OTHER PUBLICATIONS

Chothia et al (The EMBO Journal, 1986, 5/4:823-26).*
Greenspan et al (Nature Biotechnology 7: 936-937, 1999).*
Verma et al, (Nature, vol. 389, No. 6648, pp. 239-242, 1997).*
Vile et al (Gene Therapy, vol. 7, pp. 2-8, 2000).*
Guilherme L., et. al., "Towards a vaccine against rheumatic fever", Clinical & Developmental Immunology, Jun.-Dec. 2006; 13(2-4), pp. 125-132.
Abbas, A.K., et al., "Cellular and Molecular Immunology", Fourth Edition, Chapter 15, 2000, pp. 360-362.
Ellis, R. W., "New Technologies for Making Vaccines", Chapter 29, 1998, pp. 568-575.
Official Action dated Nov. 8, 2012 for Japanese Application No. 2009538555 and translation.
Supplementary European Search Report for EP Application No. 07784913.1 dated Nov. 30, 2012.
Official Action dated Jul. 23, 2013 for EP 07784913.1.
Guilherme, L., et al., "a vaccine against *S. pyogens*: Design and experimental immune response", Methods, vol. 49, Issue 4, Dec. 2009, pp. 316-321.
De Amicis, K. M., et al., "Analysis of the coverage capacity of the StreptInCor candidate vaccine against *Streptococcus pyogenes*", Vaccine 32 (2014), pp. 4104-4110.
Guilherme, L., et al., "Anti-Group A Streptococcal Vaccine Epitope", The Journal of Biological chemistry, vol. 286, No. 9, Mar. 4, 2011, pp. 6989-6998.
Postal, E., et al., "StreptInCor: A Candidate Vaccine Epitope against S. Pyogenes Infections induces Protection in Outbred Mice", PLOS One, Apr. 2013, vol. 8, Issue 4, pp. 1-6.
Guerino, M.T., et al., "HLA class II transgenic mice develop a safe and long lasting immune response against StreptInCor, an anti-group A *streptococcus* vaccine candidate", Vaccine 29 (2011), pp. 8250-8256.
Beachey, E.H., et al., "Protective Immunogenicity and T Lymphocyte Specificity of a Trivalent Hybrid Peptide Containing $NH_2$-Terminal Sequences of Types 5, 6, and 24 M Proteins Synthesized in Tandem", Journal of Experimental Medicine, vol. 166, Sep. 1, 1987, pp. 647-656.
Bessen, D., et al., "Influence of Intranasal Immunization with Synthetic Peptides Corresponding to Conserved Epitopes of M Protein on Mucosal Colonization by Group A Streptococci", Infection and Immunity, vol. 56, No. 10, Oct. 1988, pp. 2666-2672.
Bessen, D., et al., "Passive Acquired Mucosal Immunity to Group a Streptococci by Secretory Immunoglobulin A", J. Exp. Med., vol. 167, Jun. 1988, pp. 1945-1950.
Bessen, D., et al., "Synthetic Peptide vaccine Against Mucosal Colonization by Group A Streptococci", J. Immunol. 1990, 145 (4): pp. 1251-1257.
Brandt, E. R, et al., "Human antibodies to the conserved region of the M protein: opsonization of heterologous strains of group A streptococci", Vaccine, vol. 15, No. 16, 1997, pp. 1805-1812.
Cunningham, M. W., "Pathogenesis of Group A Streptococcal Infections", Clin. Microbiol. Rev., vol. 13, No. 3, Jul. 2000, pp. 470-511.
Dale, J. B., et al., "Intranasal Immunization with Recombinant Group A Streptococcal M Protein Fragment Fused to the B Subunit of *Escherichia coli* Labile Toxin Protects Mice against Systemic Challenge Infections", J. Infect. Dis. 1995, 171, April, pp. 1038-1041.
Dale, J. B., et al., "Recombinant, octavalent group A streptococcal M protein vaccine", Vaccine, vol. 14, No. 10, 1996, pp. 944-948.
Dale, J. B., "Multivalent group A streptococcal vaccine designed to optimize the immunogenicity of six tandem M protein fragments", Vaccine, 1999, 17, 1999, pp. 193-200.

(Continued)

*Primary Examiner* — Jennifer Graser
(74) *Attorney, Agent, or Firm* — Ladas & Parry LLP

(57) ABSTRACT

A method for treating rheumatic heart disease comprising administering an immunogenic composition against group A beta hemolytic streptococcus.

3 Claims, 1 Drawing Sheet

(56) References Cited

OTHER PUBLICATIONS

Dale, J. B, et al.,"New protective antigen of group A streptococci", ". J. Clin. Invest., vol. 103, 1999, pp. 1261-1268.
Dunn, L. A., et al., "Parenteral and mucosal delivery of a novel multi-epitope M protein-based group A streptococcal vaccine construct: investigation of immunogenicity in mice", Vaccine 20, 2002, pp. 2635-2640.
Fischetti, V.A., et al., "Size Variation of the M Protein in Group A Streptococci", J. Exp. Med., vol. 161, Jun. 1985, pp. 1384-1401.
Fischetti, V.A., et al., "Expression of Foreign Proteins on Gram-positive Commensal Bacteria for Mucosal Vaccine Delivery", Curr. Opin Biotech. 1993, 4, pp. 603-610.
Fischetti, V. A., "Streptococcal M Protein", Sci. Am., Jun. 1991, pp. 58-65.
Fluckiger, U., et al.,"Immunoglobulins to Group A Streptococcal Surface Molecules Decrease Adherence to and Invasion of Human Pharyngeal Cells", Infect. Immun., vol. 66, No. 3, Mar. 1998, pp. 974-979.
Guilherme, L., et al., Human Heart-Infiltrating T-Cell Clones From Rheumatic Heart Disease Patients Recognize Both Streptococcal and Cardiac Proteins, Circulation 1995, pp. 415-420.
Guilherme, L., et al., "T-Cell Reactivity against Streptococcal Antigens in the Periphery Mirrors Reactivity of Heart-Infiltrating T Lymphocytes in Rheumatic Heart Disease Patients", Infect. Immun,, vol. 69, No. 9, Sep. 2001, pp. 5345-5351.
Guilherme, L., et al., "Proinflammatory Cytokines Play a Role in the Progression and Maintenance of Valvular Lesions", Am J Pathol vol. 65, No. 5, Nov. 2004, pp. 1583-1591.
Guilherme, L., et al., "Molecular pathogenesis of rheumatic fever and rheumatic heart disease",. Exp. Rev Mol. Med., vol. 7, Issue 28, Dec. 9, 2005, pp. 1-15.
Guilherme, L., et al., "Towards a vaccine against rheumatic fever", Clin. Dev. Immunol, 13(2-4), Dec. 2006, pp. 125-132.
Kotloff, K. L., et al., "Safety and Immunogenicity of a Recombinant Multivalent Group A Streptococcal Vaccine in Healthy Adults", J. Am. Med. Assoc., vol. 292, No. 6, Aug. 11, 2004, pp. 709-715.
Kotloff, K.L., et al., "Clinical and Microbiological Responses of Volunteers to Combined Intranasal and Oral Inoculation with a *Streptococcus gordonii* Carrier Strain Intended for Future Use as a Group A *Streptococcus* Vaccine", Infect. Immun, vol. 73, No. 4, Apr. 2005, pp. 2360-2366.
Manjula, B.N., et al., "The Complete Amino Acid Sequence of a Biologically Active 197-residue Fragment of M Protein Isolated from Type 5 Group A Streptococci", The Journal of Biol. Chem., vol. 259, No. 6, Mar. 25, 1984, pp. 3686-3693.
Medaglini, D., et al., "Mucosal and systemic immune responses to a recombinant protein expressed on the surface of the oral commensal bacterium *Streptococcus gordonii* after oral colonization", Proc. Natl Acad. Sci., vol. 92, Jul. 1995, pp. 6868-6872.
McNeil, S.A., et al., "Safety and Immunogenicity of 26-Valent Group A *Streptococcus* Vaccine in Healthy Adult Volunteers", Clin. Infect. Dis., Oct. 15, 2005, pp. 1114-1122.
Miller, L., et al., "Antigenic Variation among Group A Streptococcal M Proteins", J. Biol. Chem., vol. 263, No. 12, Apr. 25, 1988, pp. 5668-5673.
Olive, C., et al., "Protection of mice from group A streptococcal infection by intranasal immunisation with a peptide vaccine that contains a conserved M protein B cell epitope and lacks a T cell autoepitope", Vaccine, 20, 2002, pp. 2816-2825.
Olive, C., et al., "Protection against group A streptococcal infection by vaccination with self-adjuvanting lipid core M protein peptides", Vaccine, 23, 2005, pp. 2298-2303.
Pruksakorn, S., et al., "Towards a vaccine for rheumatic fever: identification of a conserved target epitope on M protein of group A streptococci", The Lancet, vol. 344, Sep. 3, 1994, pp. 639-642.
Raizada, V., et al., "Tissue Distribution of Lymphocytes in Rheumatic Heart Valves as Defined by Monoclonal Anti-T Cell Antibodies", Am. J. Med., vol. 74, Jan. 1983, pp. 90-96.
Robinson, J. H., et al., "Mapping T-Cell Epitopes in Group A Streptococcal Type 5 M Protein", Infect. Immun., vol. 59, No. 12, Dec. 1991, pp. 4324-4331.
Scott, J.R., et al., "Homologous Regions within M Protein Genes in Group A Streptococci of Different Serotypes", Infect. Immun., vol. 52, No. 2, May 1986, pp. 609-612.
Scott, J.R., et al., "Relationship of M protein genes in group A streptococci", Proc. Natl. Acad. Sci., vol. 82, Mar. 1985, pp. 1822-1826.
Snitcowsky, R., "Rheumatic Fever Prevention in Industrializing Countries; Problems and Approaches", Pediatrics 97, 1996, pp. 996-998.
Vohra, H., et al., "M protein conserved region antibodies opsonise multiple strains of *Streptococcus pyogenes* with sequence variations in C-repeats", Res. Microbiol. 156, 2005, pp. 575-582.
"New Vaccines against Infectious Diseases: Research and Development Status", IVR, WHO, Apr. 2005, updated Feb. 2006, pp. 1-7.
Kemeny, E., et al., "Identification of Mononuclear Cells and T Cell Subsets in Rheumatic Valvulitis", Identification of Mononuclear Cells and T Cell subsets in Rheumatic Valvulitis, Clin. Immunol. Immunopathol., 52, 1989, pp. 225-237.

\* cited by examiner

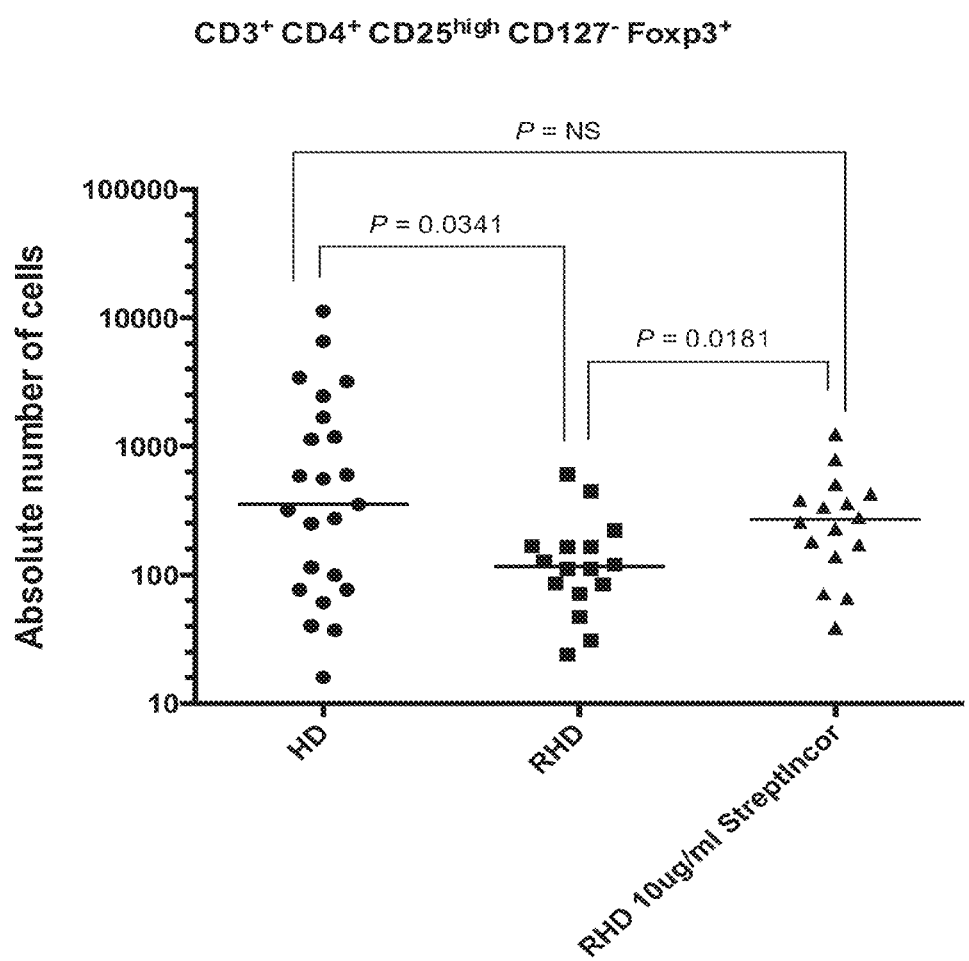

SEQUENCE LISTING

<160> NUMBER OF SEQ ID NOS: 3

<210> SEQ ID NO 1
<211> LENGTH: 55
<212> TYPE: PRT
<213> ORGANISM: ARTIFICIAL SEQUENCE
<220> FEATURE:
<223> OTHER INFORMATION: SYNTHETIC

<400> SEQUENCE: 1

Lys Gly Leu Arg Arg Asp Leu Asp Ala Ser Arg Glu Ala Lys Lys Gln
 1               5                  10                  15

Leu Glu Ala Glu Gln Gln Lys Leu Glu Glu Gln Asn Lys Ile Ser Glu
            20                  25                  30

Ala Ser Arg Lys Gly Leu Arg Arg Asp Leu Asp Ala Ser Arg Glu Ala
        35                  40                  45

Lys Lys Gln Val Glu Lys Ala
    50                  55

<210> SEQ ID NO 2
<211> LENGTH: 52
<212> TYPE: PRT
<213> ORGANISM: ARTIFICIAL SEQUENCE
<220> FEATURE:
<223> OTHER INFORMATION: SYNTHETIC

<400> SEQUENCE: 2

Lys Gly Leu Arg Arg Asp Leu Asp Ala Ser Glu Arg Ala Lys Lys Gln
 1               5                  10                  15

Leu Glu Ala Glu Gln Gln Lys Leu Glu Glu Gln Asn Lys Ile Ser Glu
            20                  25                  30

Ala Ser Arg Lys Gly Leu Arg Arg Asp Leu Asp Ala Ser Arg Glu Ala
        35                  40                  45

Lys Lys Gln Val
    50

<210> SEQ ID NO 3
<211> LENGTH: 165
<212> TYPE: DNA
<213> ORGANISM: ARTIFICIAL SEQUENCE
<220> FEATURE:
<223> OTHER INFORMATION: SYNTHETIC

<400> SEQUENCE: 3
aaaggccttc gccgtgattt agacgcatca cgtgaagcta agaagcaatt agaagctgaa       60
caacaaaaac ttgaagaaca aaacaagatt tcagaagcaa gtcgcaaagg ccttcgccgt      120
gatttagacg catcacgtga agctaagaaa caagttgaaa aagct                      165

THERAPEUTIC APPLICATION OF *S. PYOGENES* C-TERMINAL PEPTIDE

CROSS REFERENCE APPLICATIONS

This application is a continuation-in-part application of U.S. patent application Ser. No. 12/516,754 filed Jan. 19, 2010, now U.S. Pat. No. 8,642,049, published as US 2010-0183518A1 on Jul. 22, 2010, the subject matter of which is incorporated by reference.

BACKGROUND OF THE INVENTION

Group A Streptococci (GAS) diseases remain a major public health problem in developing countries, reaching 600 million registered cases with 233,000 deaths per year. Rheumatic fever (RF) is considered an autoimmune disease resulting from the defense immune response triggered against the group A beta hemolytic streptococcus, or *S. pyogenes*. In some individuals (those with susceptibility to the illness), it produces an aggressive response against the organism's own proteins through biological mimicry mechanisms. If not treated properly they can lead to autoimmune post-streptococcal sequels such as RF that affects mainly children and teenagers. Rheumatic heart disease (RHD) is the most serious sequel of RF, leading to progressive and permanent heart valvular lesions.

The M-protein sequences of streptococcus were analyzed and published in the 1980s (Manjulae Philipis, 1984, and Miller et al, 1998), and permitted great advances in the knowledge of the regions capable of triggering the illness.

The M-protein contains regions of repetitions of amino acid residues, and is subdivided into an amino-terminal portion and a carboxy-terminal portion. In the amino-terminal portion are the residues of amino acids that define the streptococcus serotype. The carboxy-terminal portion (C-portion) is quite conserved among the different serotypes and has groups of amino acids that repeat themselves more than once (Fischetti, 1991).

Several segments of the amino-terminal region are involved in the triggering of RF and/or chronic RHD, especially through cross-reaction with proteins of the cardiac tissue (Cunningham, 2000 and Guilherme et al, 2005).

Several events lead to RF and RHD that leads to permanent heart-tissue lesions. Several genes are involved in the development of both RF and RHD. The inflammatory process that results from *S. pyogenes* infection involves the activation of several molecules such as VCAM and ICAM, which play a role in the migration of leukocytes to the heart, particularly to the valves. Specific chemokines, such as CXCL3/MIP1α as well as CCL1/I309 and CXCL9/Mig, attract T cells to the myocardium and valves, respectively and are responsible for intense inflammatory reactions that will result in the autoimmune heart-tissue lesions in RHD patients. These reactions are mediated by both the B- and T-cell responses that begin at the periphery, followed by the migration and infiltration of T-cell clones to the heart. These cells recognize streptococcal antigens and human tissue proteins. Molecular mimicry between streptococcal M protein and human proteins has been proposed as the triggering factor leading to autoimmunity in RF and RFID (Cunningham 2000 and Guilherme 2011). The production of cytokines from peripheral and heart-infiltrating mononuclear cells suggests that T helper 1 (Th1) and Th17 cytokines are the mediators of RHD heart lesions. The low numbers of IL-4-producing cells in the valvular tissue and also the low numbers of T regulatory cells in the peripheral blood might contribute to the maintenance and progression of the valve lesions. The identification of the StreptInCor epitope (Guilherme, et al., 2011) that presents the capacity of inducing T cells that regulate the inflammatory process in the heart opens a perspective of a new treatment for RF and RHD.

SUMMARY OF THE INVENTION

An aspect of this invention is a method for treating rheumatic heart disease using a peptide derived from the C-terminal protein of the Group A Beta Hemolytic Streptococcus.

Another aspect of the invention is method for treating rheumatic heart disease using the peptide of SEQ ID NO:1.

Another aspect of the invention is method for treating rheumatic heart disease using the peptide of SEQ ID NO:2.

Still another aspect of the invention is the use of the peptide of SEQ ID NO:1 to induce production of T-regulatory cells.

Still another aspect of the invention is the use of the peptide of SEQ ID NO:2 to induce production of T-regulatory cells.

An aspect of this invention is a method for treating rheumatic heart disease using StreptInCor.

Still another aspect of the invention is the use of StreptInCor to induce production of T-regulatory cells.

A further aspect of the invention is a method of treating autoimmune heart-tissue lesions of Rheumatic heart disease.

A more complete appreciation of the present invention and many of the attendant advantages thereof will be readily understood by reference of the following detailed description and with the accompanying drawing.

BRIEF DESCRIPTION OF THE DRAWINGS

FIG. 1 shows that StreptInCor induces the production Natural T-regulatory cells (T-reg).

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. The methods and techniques of the present invention are generally performed according to methods known in the art.

When the terms "one," "a," or "an" are used in this disclosure, they mean "at least one" or "one or more,", unless otherwise indicated. Further, unless otherwise required by context, singular terms shall include pluralities and plural terms shall include the singular unless the content clearly dictates otherwise.

All publications, patents and patent applications cited herein, whether supra or infra, are hereby incorporated by reference in their entirety.

A StreptInCor epitope derived from C-terminal, region of the M5 protein has a sequence of 55 amino acids which is:

```
                                          (SEQ ID NO: 1)
KGLRRDLDASREAKKQLEAEQQKLEEQNKISEASRKGLRRDLDASREAKK

QVEKA
```

StreptInCor epitope can also have the SEQ ID NO:2 Lys-Gly-Leu-Arg-Arg-Asp-Leu-Asp-Ala-Ser-Glu-Arg-Ala-Lys-Lys-Gln-Leu-Ala-Glu-Gln-Gln-Lys-Leu-Glu-Glu-Gln-Asn-Lys-Ile-Ser-Glu-Ala-Ser-Arg-Lys-Gly-Leu-Arg-Arg-Asp-Leu-Asp-Ala-Ser-Arg-Glu-Ala-Lys-Lys-Gln-Val which is 52 amino acids.

```
                                            (SEQ ID NO: 3)
AAAGGCCTTC  GCCGTGATTT  AGACGCATCA  CGTGAAGCTA

AGAAGCAATT  AGAAGCTGAA  CAACAAAAAC  TTGAAGAACA

AAACAAGATT  TCAGAAGCAA  GTCGCAAAGG  CCTTCGCCGT

GATTTAGACG  CATCACGTGA  AGCTAAGAAA  CAAGTTGAAA

AAGCT
```

The tridimensional molecular structure of StreptInCor was elucidated by nuclear magnetic resonance showing that its structure is composed of two microdomains linked by an 18-residue α-helix. The folding and refolding mechanism of StreptInCor proceeds as a reversible process by using circular dichroism—meaning that the StreptInCor structure can be reverted to its original state in a wide range of temperatures, pH, and concentration of chaotropic agents. These are important properties for a vaccine (Guilherme, 2011).

A method for preparing SEQ ID NO:1 is described in the example. SEQ ID NO:1 and SEQ ID NO:2 can be prepared in other ways known to those of skill in the art.

Additional information about StreptInCor is found in US Patent Application Publication 2010-0183518A1.

StreptInCor peptide is capable of inducing in vitro the proliferation of a type of cells that present the capacity of regulating the inflammation in RHD as described below. T regulatory cells (Tr1) or (Treg) are identified by several cellular markers (CD3, CD4, CD25, CD127 and Foxp3) and by the secretion of specific cytokines such as IL-10 and TGF-beta. (Battaglia et al, 2006).

The observation of a possible therapeutic effect of StreptInCor to treat RHD was based on in vitro experiments using T cell lines derived from heart-tissue of RHD patients that underwent surgery for valve correction or replacement that showed that StreptInCor—derived peptides were able to induce in vitro the production of IL-10 by some T cell lines (6 out of 29) (20.7%) and clones (7/49) (14.3%). These results strongly indicated the capacity of StreptInCor for inducing Treg cells.

In addition, other experiments confirm this property and showed that StreptInCor peptide was also able to induce the proliferation of Treg cells of peripheral blood of normal individuals and RHD patients, thus indicating that the StreptInCor epitope presents a property of inducing T regulatory cells by increasing the numbers of Treg cells and leading to a balance of normal cells (FIG. 1).

The capacity of regulatory T cells induction by StreptInCor, through identification of specific cellular markers (CD3, CD4, CD25, CD 127 and Foxp3) for this subset of T cell by gene expression and flow citometry is described. Peripheral blood mononuclear cells (PBMC) of RHD and controls were stimulated with 10 μg/ml of StreptInCor synthetic peptide. StreptInCor induced the increase of natural T regulatory cells (nTreg) in PBMC in both groups (P=0.0043 and 0.0006, respectively). The number of nTreg cells in PBMC from DRC patients before the stimulus is lower than that observed in PBMC from controls (P=0.0341).

These results show the ability of StreptInCor of regulating the autoimmune reactions through the heart (myocarditis and valvulitis), and consequent amelioration of the heart-tissue rheumatic lesions. StreptInCor of SEQ ID NO:1 or SEQ ID NO:2 is able to regulate the autoimmune heart-tissue lesions without triggering autoimmune disease.

The vaccine epitope of StreptInCor induced systemic protective immune response in murine models.

In particular, the invention relates to a method of using StreptInCor or pharmaceutical composition thereof, for use as a medicament, preferably in treatment, alleviation or prophylaxis of heart-tissue rheumatic lesions resulting from RHD. The invention also relates to methods of inducing Treg cells leading to methods for treating, alleviating or preventing heart-tissue rheumatic lesions resulting from RHD comprising administering an effective amount of StreptInCor, SEQ ID NO:1, SEQ ID NO:2 or immunogenic or pharmaceutical composition thereof.

The invention also provides pharmaceutical compositions comprising StreptInCor, a peptide of SEQ ID NO:1, a peptide of SEQ ID NO:2 or an immunogenic composition thereof, in a formulation in association with one or more pharmaceutically acceptable excipient(s). The term excipient is used herein to describe any ingredient other than the active ingredient. The choice of excipient(s) will to a large extent depend on factors such as the particular mode of administration, the effect of the excipient on solubility and stability, and the nature of the dosage form. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

Any method for administering peptides, or proteins accepted in the art may suitably be employed for the peptides or proteins of the invention.

The pharmaceutical compositions of the invention are suitable for parenteral, oral, or other suitable method such as intranasal or inhalation. As used herein, parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ.

Formulations of a pharmaceutical composition suitable for parenteral administration typically generally comprise the active ingredient combined with a pharmaceutically acceptable carrier, such as sterile water or sterile isotonic saline.

A pharmaceutically effective dose or therapeutically effective dose is that dose required to treat or prevent, or alleviate one or more disorders related to RHD. The effective dose depends on inter alia the specific compound to administer, the severity of the symptoms, the susceptibility of the subject to side effects, the composition used, the route of administration, the type of mammal being treated, the physical characteristics of the specific mammal under consideration such as health and physical condition, concurrent medication, and other factors that those skilled in the medical arts will recognize.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The frequency of administration can vary depending on any of a variety of factors, e.g., severity of the symptoms, degree of immunoprotection desired, whether the composition is used for prophylactic or curative purposes, etc.

EXAMPLES

The following example is put forth so as to provide those of ordinary skill in the art with a complete disclosure and description of how to make and use the present invention, and are not intended to Limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Standard abbreviations are used.

Example 1

This peptide was obtained by chemical synthesis in a batch mode, using Fmoc chemistry and in situ activation of the amino acids with HOBt/HBTU-1-hydroxybenzotriazole/{N-[(1H-benzotriazol-1-yl)(dimethylamino)methylene}-N-methylmethanaminium hexafluorophosphate N-oxide}-. The peptide was synthesized using NovaSyn™ TGR resin and DMF (N,N-dimethylformamide) as the sole solvent. The resin was contained in a fixed bed type reactor of an Advanced ChemTech robotic bench-top multiple peptide synthesis system model APEX-396.

The Fmoc-amino acid derivatives were dissolved in a 0.4 M HOBt/DMF solution in order to obtain an equimolar amino acid/HOBt solution. This solution was automatically added to the reaction wells containing the resin, followed by stepwise addition of HBTU and N-methylmorpholine. Removal of the Fmoc group from the N-terminus of the resin-bound peptide chain was achieved by treating the peptidyl resin with a 2 M piperidine/DMF solution. After removal of the Fmoc group, the peptide resin was prepared for cleavage. At this stage, the resin was thoroughly washed with DMF, acetic acid and then DCM several times. The peptide resin was dried under high vacuum for 4 h, and the prepared peptide resin was cleaved with a TFA-trifluoroacetic acid/TIS (triisopropylsilane)/water cleavage cocktail.

The crude peptide was extracted several times with concentrated TFA and lyophilized after the addition of water. The peptide products were analyzed by reverse phase HPLC on a Shim-pack CLC-ODS-M column. The HPLC system consisted of two LC-10AT VP pumps, a SPD-10AV VP UV-VIS detector set at 214 nm, and a SIL-10AF auto-injector. The samples were submitted to chromatography at a flow rate of 1 ml/mm using 0.1% (v/v) $H_3PO_4$ aqueous solution as solvent A and 90% (v/v) acetonitrile 9.9% (v/v) water and 0.1% (v/v) $H_3PO_4$ as solvent B, with a linear gradient from 15-95% (v/v) of B solvent in 15 min. Preparative HPLC was performed using an HPLC system AEKTA basic, consisting of four pump heads of the 903 pump family in two pump modules, a UV-absorption monitor model UV-900 set at 214 nm and at 231 nm, a fraction collector FRAC-900, and a Shim-pack PREP-ODS column (20 mm i.d.×25 cm). The wave length of 231 nm was used to slow down the signal of the detector that controls the fraction collector. The samples were submitted to chromatography at a flow rate of 2 ml/min using 0.1% (v/v) TFA aqueous solution as solvent A and 90% (v/v) acetonitrile 9.9% (v/v) water and 0.1% (v/v) TFA as solvent B, with a linear gradient from 0-100% (v/v) B in 50 min. Peptide purity was the amount of correct peptide relative to all analytes that absorbed at 214 nm, where the peptide bond absorbs. These contaminants were most likely deletions, truncations or incompletely deprotected sequences, etc. Peptide purity does not take into account water and salts that are usually present in the sample. Molecular weight was determined using an Ettan MALDI-ToF Pro Mass Spectrometer with the HPLC-purified products. A purity degree of 99.5% was obtained as shown in FIG. 1 of (Guilherme et al, 2006).

REFERENCES

1. Cunningham M W. Pathogenesis of group A streptococcal infections. *Clin Microbiol Ver* (2000) 13, 470-511.
2. Guilherme, L, Köhler, K F, and Kalil, J. Rheumatic heart disease: mediation by complex immune events. *Adv Clin Chem* (2011) 53:31-50.
3. Guilherme L, Alba M P, Ferreira F M, Oshiro S E, Higa F, Patarroyo M E, et al. Anti-group A streptococcal vaccine epitope: structure, stability, and its ability to interact with HLA class II molecules. J Biol Chem (2011) 286(9):6989-98.
4. Battaglia M, Stabilini A, Migliavacca B, Horejs-Hoeck J, Kaupper T, Roncarolo, M G. Rapamycin promotes expansion of functional CD4+CD25+FOXP3+ regulatory T cells of both healthy subjects and type 1 diabetic patients. J Immunol. 2006 Dec. 15; 177(12):8338-47.

US PATENT DOCUMENTS

U.S. Pat. No. 6,602,507, filed on Jan. 6, 1995 and granted on Aug. 5, 2003;
U.S. Pat. No. 6,716,433, filed on Sep. 10, 1998 and granted on Apr. 6, 2004;
U.S. Pat. No. 6,358,704, filed on Jan. 28, 1999, granted on Mar. 19, 2002.

OTHER REFERENCES

1. Beachey E H, Seyer J M, Dale J B: "Protective immunogenecity and T lymphocyte specificity of a trivalent hybrid peptide containing NH2-terminal sequences of types 5, 6 and 24 M proteins synthesized in tandem". J. Exp. Med. 1987; 166:647-656.
2. Bessen D, Fischetti V A: "Influence of intranasal immunization with synthetic peptides corresponding to conserved epitopes of M protein on mucosal colonization by group A streptococci". Infect. Immun. 1988; 565: 2666-2672.
3. Bessen D, Fischetti V A: "Passive acquired mucosal immunity to group A streptococci by secretory immunoglobulin". A. J. Exp. Med. 1988; 167: 1945-1949.
4. Bessen D, Fischetti V A: "Synthetic peptide vaccine against mucosal colonization by group A streptococci. I. protection against a heterologous M serotype with shared C repeated region epitopes". J. Immunol. 1990; 145 (4): 1251-12.
5. Brandt E R, Hayman W A, Currie B, Pruksakorn S, Good M F: "Human antibodies to the conserved region of the M protein: opsonization of heterologous strains of group A streptococci". Vaccine 1997; 15: 1805-1812.
6. Cunningham, M. W. (2000): "Pathogenesis of group A streptococcal infections". Clin. Microbiol. Rev. 470-511.
7. Dale J B, Chang E C: "Intranasal immunization with recombinant group A streptococcal M fragment fused to the B subunit of *Escherichia coli* labile toxin protects mice against systemic challenge infections". J. Infect. Dis. 1995; 171: 1038-1041,
8. Dale J B, Chang E Y, Lederer J W. "Recombinant tetravalent group A streptococcal M protein vaccine". J. Immunol. 1993, 151 (4): 2188-2194.

9. Dale J B, Simmons M, Chiang E C, Chiang E Y: "Recombinant, octavaient group A streptococcal M protein vaccine". Vaccine. 1999, 14 (10): 944-948.
10. Dale, J B: "Multivalent group A streptococcal vaccine designed to optimize the immunogenecity of six tandem M protein fragments". Vaccine, 1999, 17:193-200.
11. Dale, J B, Chiang E Y., Liu S., Courtney H S., Hasty, D L. "New protective antigen of group A streptococci". J. Clin. Invest. 1999, 103:1261-1268.
12. Dunn, L A, McMillan D J, Batzloff M, Zeng W, Jackson D C J, Upcroft J A, Upcroft P, Olive C: "Parenteral and mucosal delivery of a novel multi-epitope M protein-based group A streptococcal vaccine construct: investigation of immunogenecity in mice". Vaccine, 2002, 20: 2635-2640.
13. Fischetti V A, Jones K F, Scott J R.: "Size variation of the M protein in group A streptococci". J. Exp. Med. 1985, 161: 1384-1401.
14. Fischetti V A, Medaglini D, Oggioni M, Pozzi G: "Expression of foreign proteins on gram-positive commensal bacteria for mucosal delivery". Curr. Opin Biotech. 1993, 4:503-610.
15. Fischetti, V.: "Streptococcal M protein". Sci. Am.: 1991 264(6): 32-39.
16. Fluckiger, U.; Jones K F; Fischetti, V A.: "Immunoglobulins to group A streptococcal surface molecules decrease adherence to and invasion of human pharyngeal cells". Infect, Immun. 1998, 66: 974-979.
17. Guilherme L, Cunha-Neto E, Coelho V, Snitcowsky R, Pomerantzeff P. M A, Assis R V, Pedra F, Neumann J, Goldberg A, Patarroyo M E, Pillegi F, Kalil J: "Human-infiltrating T cell clones from rheumatic heart disease patients recognize both streptococcal and cardiac proteins". Circulation 1995; 92: 415-420.
18. Guilherme, L., Oshiro, S. E., Fae, K. C., Cunha-Neto, E., Renesto, G et al: "T cell reactivity against streptococcal antigens in the periphery mirrors reactivity of heart infiltrating T lymphocytes in rheumatic heart disease patients". Infect. Immun, 2001, 69:5345-5351.
19. Guilherme L., P. Cury, L. M. Demarchi, V. Coelho, L. Abel, A P. Lopez, S. E. Oshiro, S. Aliotti, E. Cunha-Neto, P. M. Pomerantzeff, A. C. Tanaka and J. Kalil: Rheumatic heart disease: proinflammatory cytokines play a role in the progression and maintenance of valvular lesions. Am J Pathol, 2004, 165:1583-91.
20. Guilherme, L Fae, K C, Oshiro, S E, Kalil, J: Molecular pathogenesis of Rheumatic fever and rheumatic heart disease. Exp. Rev Mol Med, 2005, 7(28): 1-15.
21. Guilherme, L Fae, K C, Higa F, Chaves, L, Oshiro, S E, Freschi de Barros. S, Puschel. C, Juliano, M A, Tanaka, A C, Spina, G, Kalil, J: Towards a vaccine against rheumatic fever. Clin Dev Immunol, 2006, XX 1-8.
22. Kemeny, E., Grieve, T., Marcus, R., Sareli, P., Zabriskie, J B: "Identification of mononuclear cells and T cell subsets in rheumatic valvulitis". Clin. Immunol. Immunopathol. 1989, 52:225-237.
23. Kotloff K I Correti M, Palmer K, Campbell J D, Reddish M A, Hu M C, Wasserman S S, Dale J B: "Safety and immunogenecity of a recombinant multivalent group A streptococcal vaccine in healthy adults". J. Am, Med. Assoc (JAMA), 2004, 11: 709-715.
24. Kotloff K L, Wasserman S S, Jones K F, Livio S I Hruby D E I Franke C A, Fischetti V A: Clinical and microbiological responses of volunteers to combined intranasal and oral inoculation with a Streptococcus gordonii carrier strain intended for future use as a group A streptococcus vaccine. Infect Immun, 2005, 73(4):2360-6.
25. Manjula, B. N., Acharya, A. S., Mische, M. S., Fairwell, T. and Fischetti, V. A.: "The complete amino acid sequence of a biologically active 197-residue fragment of M protein isolated from type 5 group A streptococci". J. Biol, Chem., 1984, 259, 3686-3693.
26. Medaglini D, Pozzi G, King T P, Fischetti V A: "Mucosal and systemic immune response to a recombinant protein expressed on the surface of the oral commensal bacterium Streptococcus gordoni after oral colonization". Proc. Natl Acad. Sci. USA, 1995, 92: 6868-6872.
27. McNeil S A, Halperin S A, Langley J M, Smith B, Warren A, Sharratt G P, Baxendale D M, Reddish M A, Hu M C, Stroop S D, Linden J, Fries L F, Vink P E, Dale J B.: Safety and immunogenicity of 26-vaient group a streptococcus vaccine in healthy adult volunteers. Clin Infect Dis, 2005, 41 (8): 1114-22.
28. Miller, L. C., Gray, E. D., Beachey, E. H. and Kehoe, M. A.: "Antigenic variation among group A streptococcal M proteins: nucleotide sequence of the serotype 5 M protein gene and its relationship with genes encoding types 6 and 24 M proteins". J. Biol. Chem., 1988, 263, 5668-5673,
29. Olive C, Clair T, Yarwood P, Good M: "Protection of mice from group A streptococcal infection by intranasal immmunisation with a peptide vaccine that contains a conserved M protein B cell epitope and lacks a T cell autoepitope". Vaccine, 2002, 20: 2816-2825.
30. Olive C, Hsien K, Horvath A, Clair T, Yarwood P, Toth I I Good M F. Protection against group A streptococcal infection by vaccination with self-adjuvanting lipid core M protein peptides. Vaccine, 2005 23(17-18):2298-303.
31. Pruksakorn S, Currie B, Brandt E R, Martin D I Galbraith A, Phornphutkul C H, Hunsakunachai S, Manmontri A, Good M F: "Towards a vaccine for rheumatic fever: Identification of a conserved target epitope on M protein of group A streptococci". The Lancet, 1994; 344:639-642.
32. Raizada, V., Williams, R. C. Jr., Chopra, P., Gopinath, N., Prakash, K. et al; "Tissue distribution of lymphocytes in rheumatic heart valves as defined by monoclonal anti-T cells antibodies". Am, J. Med., 1983, 74, 90-96.
33. Robinson, J. H., Atherton, M. C, Goodacre, J. A., Pinkney, M., Weightman, H. and Kehoe, M. A. (1991): "Mapping T-cell epitopes in group A streptococcal type 5 M protein". Infect. Immun. 59, 4324-4.
34. Scott, J R.; Hollingshead S K.; Fischetti V A: "Homologous regions within M protein genes in group A streptococci of differents serotypes". Infect. Immun. 1986, 52:609-613.
35. Scott, J R.; Pulliam, W N.; Hollingshead S K.: "Fischetti V A. Relationship of M protein genes in group A streptococci". Proc. Natl. Acad. Sci. USA. 1985, 82: 1822-1827.
36. Snitcowsky, R.: "Rheumatic fever prevention in industrializing countries: problems and approaches". Pediatrics. 1996, 97(6): 996-998.
37. 37. Vohra H, Dey N, Gupta S, Sharma A K, Kumar R, McMillan D, Good M F.: M protein conserved region antibodies opsonise multiple strains of Streptococcus pyogenes with sequence variations in C-repeats. Res Microbiol, 2005, 156(4):575-82.
38. WHO, IVR.: New vaccines against infectious diseases: research and development status, April, 2005, updated February 2006.

The invention claimed is:

1. A method of treating rheumatic heart disease comprising administering a composition comprising SEQ ID NO:2 to a subject in need thereof.

2. The method according to claim 1, wherein administration of the composition comprising SEQ ID NO:2 induces production of IL-10.

3. The method according to claim 1, wherein administration of the composition comprising SEQ ID NO:2 induces proliferation of Treg cells.

* * * * *